(12) United States Patent
Weinberg

(10) Patent No.: US 6,628,984 B2
(45) Date of Patent: Sep. 30, 2003

(54) HAND HELD CAMERA WITH TOMOGRAPHIC CAPABILITY

(75) Inventor: Irving N. Weinberg, Bethesda, MD (US)

(73) Assignee: PEM Technologies, Inc., Bethesda, MD (US)

( * ) Notice: Subject to any disclaimer, the term of this patent is extended or adjusted under 35 U.S.C. 154(b) by 166 days.

(21) Appl. No.: 09/833,110

(22) Filed: Apr. 11, 2001

(65) Prior Publication Data

US 2001/0056234 A1 Dec. 27, 2001

Related U.S. Application Data

(60) Provisional application No. 60/196,654, filed on Apr. 12, 2000, and provisional application No. 60/240,727, filed on Oct. 16, 2000.

(51) Int. Cl.$^7$ ................................................ A61B 6/00
(52) U.S. Cl. ........................ 600/436; 600/407; 600/425; 378/4; 250/363.02; 250/363.1; 250/370.09
(58) Field of Search ................ 600/436, 407, 600/425, 429; 250/363.1, 363.02, 370.09; 378/4, 21

(56) References Cited

U.S. PATENT DOCUMENTS

| | | | |
|---|---|---|---|
| 3,714,429 A | * 1/1973 | Mozley et al. | 250/363.04 |
| 4,197,460 A | * 4/1980 | Anger | 250/363.02 |
| 4,506,374 A | * 3/1985 | Flynn | 378/2 |
| H12 H | * 1/1986 | Bennett et al. | 250/363.09 |
| 5,252,830 A | 10/1993 | Weinberg | |
| 5,270,549 A | * 12/1993 | Engdahl | 250/505.1 |
| 5,323,006 A | 6/1994 | Thompson et al. | |
| 5,519,221 A | 5/1996 | Weinberg | |
| 5,734,384 A | * 3/1998 | Yanof et al. | 345/424 |
| 5,813,985 A | * 9/1998 | Carroll | 600/436 |
| 5,965,891 A | 10/1999 | Weinberg | |
| 6,064,904 A | * 5/2000 | Yanof et al. | 600/414 |
| 6,198,470 B1 | 3/2001 | Agam et al. | |
| 6,207,111 B1 | 3/2001 | Weinberg | |
| 6,229,145 B1 | 5/2001 | Weinberg | |
| 6,236,880 B1 | * 5/2001 | Raylman et al. | 600/436 |

OTHER PUBLICATIONS

William R. Brown, Ph.D, Dixon M. Moody, MD, Venkata R. Challa, MD, David A Stump, PhD, and John W. Hammon, MD, Longer Duration of Cardiopulmonary Bypass is Associated with Greater Number of Cerebral Microemboli, Stroke, 2000; 31:707–713.

B. Barry, J.C. Lucet, M.J. Kosmann, P. Gehanno, Risk Factors for Surgical Wound Infections in Patients Undergoing Head and Neck Oncologic Surgery, Acta otor–rhino–laryngologica belg., 1999, 53, pp.241–244.

Hans Jacobsson, Göran Wallin, Sigbritt Werner, Stig A. Larsson, Technetium–99m Methoxyisobutylisonitrile Localizes an Ectopic ACTH–Producing Tumour: Case Report and Review of the Literature, European Journal of Nuclear Medicine, vol. 21, No. 6, Jun. 1994, pp. 582–586.

(List continued on next page.)

Primary Examiner—Marvin M. Lateef
Assistant Examiner—Barry Pass
(74) Attorney, Agent, or Firm—Katten Muchin Zavis Rosenman

(57) ABSTRACT

A tomographic imaging system includes a moveable detector or detectors capable of detecting gamma radiation; one or more position sensors for determining the position and angulation of the detector(s) in relation to a gamma ray emitting source; and a computational device for integrating the position and angulation of the detector(s) with information as to the energy and distribution of gamma rays detected by the detector and deriving a three dimensional representation of the source based on the integration. A method of imaging a radiation emitting lesion located in a volume of interest also is disclosed.

37 Claims, 10 Drawing Sheets

OTHER PUBLICATIONS

MJ Weldon, AM Masoomi, AJ Britten, J Gane, CJ Finlayson, AEA Joseph, JD Maxwell, Quantification of Inflammatory Bowel Disease Activity Using Technetium–99m HMPAO Labelled Leucocyte Single Photon Emission Computerised Tomography (SPECT), Gut 1995; 36:243–250.

C.H. Kao, M.D., H.T. Lin, B.S.c., Y.L. Wang, M.Sc., S.J. Wang M.D., and T.J. Liu, M.D., Tc–99m HMPAO–Labeled WBC Scans to Detect Appendicitis in Women, Clinical Nuclear Medicine, vol. 21, No. 10. pp. 768–771.

Ulf Öhrvall, M.D., Jan E. Westlin, M.D., Sten Nilsson, M.D., Claes Juhlin, M.D., Jonas Rastad, M.D., Hans Lundqvist, Ph.D., Göran Åkerström, M.D., Intraoperative Gamma Detection Reveals Abdominal Endocrine Tumors More Efficiently than Somatostatin Receptor Scintigraphy, Sixth Conference on Radioimmunodetection and Radiommunotherapy of Cancer, Cancer Supplement, Dec. 15, 1997, vol. 80, No. 12, pp. 2490–2494.

Joseph A. Kuhn, MD, Raffael M. Corbisiero, MD, Robert R. Buras, MD, Robert G. Carroll, MD, Lawrence D. Wagman, MD, Latresia A. Wilson, PhD, Dave Yamauchi, MD, Merle M. Smith, RN, Russell Kondo, J. David Beatty, MD, Intraoperative Gamma Detection Probe with Presurgical Antibody Imaging in Colon Cancer, Arch Surg, vol. 126, Nov. 1991, pp. 1398–1403.

Roy P. Walmsley, PhD, Perry Kimber, MSc, and Elsie Culham, PhD, The Effect of Initial Head Position on Active Cervical Axial Rotation Range of Motion in Two Age Populations, SPINE, vol. 21, No. 21, pp. 2435–2442.

Roy P. Walmsley, PhD. Perry Kimber, MSc, and Elsie Culham, PhD, The Effect of Intial Head Position on Active Cervical Axial Rotation Range of Motion in Two Age Populations, Spine, vol. 21, No. 21, pp. 2435–2442.

William R. Osebold, MD, Edward L. Lester, MD, John H. Hurley, MD, and Ronald L. Vincent, MD, Intraoperative Use of the Mobile Gamma Camera in Localizing and Excising Osteoid Osteomas of the Spine, Spine, vol. 18, No. 13, pp. 1816–1828.

Fadi F. Haddad, MD, Steven C. Shivers, PhD, and Douglas S. Reintgen, MD, Historical Perspectives and Future Applications, Radioguided Surgery, Surgical Oncology Clinics of North America, vol. 8, No. 3, Jul. 1999, 10 pp. 391–400.

H. Kudrolli, W. Worstell, and V. Zavarzin, An Inverse Monte Carlo Procedure for 3–D PET Image Reconstruction, Proceedings IEEE Nucl. Sci. Symp. 1988, 5 pages.

Irving Weinberg, Stan Majewski, Andrew Weisenberger, Allen Markowitz, Luigi Aloj, Lukasz Majewski, David Danforth, James Mulshine, Kenneth Cowan, JoAnne Zujewski, Catherine Chow, Elizabeth Jones, Victoria Chang, Wendie Berg and Joseph Frank, Preliminary Results for Positron Emission Mammography: Real–time Funcation Breast Imaging in a Conventional Mammography Gantry, European Journal of Nuclear Medicine, vol. 23, No. 7, Jul. 1996.

C.J. Thompson, K. Murthy, I.N. Weinberg, F. Mako, Feasibility Study for Positron Emission Mammography, Medical Physics, vol. 21, No. 4, Apr. 1994, p. 529–538.

Martin Hanke, Andreas Neubauer, Otmar Scherzer, A Convergence Analysis of the Landweber Iteration for Nonlinear Ill–posed Problems, Numer. Math. 72:21–37 (1995).

Donald W. Wilson and Benjamin M. W. Tsui, Noise Properties of Filtered–Backprojection and ML–EM Reconstructed Emission Tomographic Images, IEEE Transactions on Nuclear Science, vol. 40, No. 4, Aug. 1993, pp. 1198–1203.

G. Muehllehner, M.P. Buchin, J.H. Dudek, Performance Parameters of a Positron Imaging Camera, IEEE Transactions on Nuclear Science, vol. NS–23, No. 1, Feb. 1976, pp. 528–537.

C. Luyken, G. Hilderbrandt, B. Krisch, K. Scheidhauer, and N. Klug, Clinical Relevance of Somatostatin Receptor Scintigraphy in Patients with Skull Base Tumours, Acta Neurochir (1996) [Supp.] 65:102–104.

R. Gennari, H.S. Stoldt, M. Bartolomei, S. Zurrida, A. Testori, G. Mazzarol, G. Paganelli and U. Veronesi, Sentinel Node Localisation: A New Prospective in the Treatment of Nodal Melanoma Metastases, International Journal of Oncology 15:25–32, 1999.

D.W. Wilson, Decomposition of Images and Objects into Measurement and Null Components, Mar. 16, 1998, vol. 2, No. 6, Optics Express 254–260.

Goldstein, Classical Mechanics, pp. 107–109, Addison–Wesley, Reading, MA (1950).

* cited by examiner

HAND HELD CAMERA WITH TOMOGRAPHIC CAPABILITY

This application claims the benefit of U.S. Provisional Patent Application No. 60/196,654 filed Apr. 12, 2000. This application also claims the benefit of U.S. Provisional Patent Application No. 60/240,727 filed Oct. 16, 2000.

BACKGROUND OF THE INVENTION

The present invention relates to a tomographic imaging system and method.

Intraoperative visualization of target lesions and overlying tissues can reduce the time and invasiveness of surgical procedures, which results in cost savings and reductions in surgical complications. Currently available gamma-ray surgical guidance tools include gamma-ray sensitive nonimaging "probes". These non-imaging gamma-ray probes resemble classic Geiger counters in appearance. Most modern nonimaging gamma-ray probes have enhanced directional responses (unlike Geiger counters) so that the surgeon can point to structures of interest, and feature a user interface that generates squawks and whistles instead of clicks. Gamma-ray probes are utilized in surgical procedures in which patients are administered radioactive substances prior to surgery. The radioactive substances can be injected systemically, as in the case of tumor-seeking radiotracers (e.g., carcinoembryonic antigen (CEA) analogues for ovarian cancer surgery). In the case of systemic injection, the surgeon's goal is to detect occult nests of cancer cells for removal to increase the chances for complete tumor kill during chemotherapy. The radioactive substances can also be injected locally, in order to delineate lymphatic drainage patterns (i.e., sentinel node procedure).

Gamma-ray surgical guidance has been attempted for several tumor types. For example, neuroendocrine tumors have been detected intraoperatively with nonimaging probes, even when the tumors were initially missed on magnetic resonance images ("MRI") and computer tomography ("CT") scans. Colon cancer deposits also have been detected with intraoperative nonimaging probes.

Once cancer has been identified, lymphatic drainage patterns can be studied to stage the patient's disease. For this application, the radioactive substances are injected locally near the site of a known primary cancer, so that the drainage patterns to local lymph nodes can be ascertained. According to the "sentinel node" theory, a single node stands at the entryway to more distant sites. Subscribers to this theory attempt to identify and remove this sentinel node. By examining whether the sentinel node contains tumor cells, pathologists aim to predict whether the tumor is likely to have spread to distant locations. Sampling of the sentinel node is preferable to the traditional surgical practice of removing entire blocks of nodes, because of the reduced levels of complications following node removal.

Gamma-ray probes have become the standard of care for surgical procedures involving melanoma in the extremities (i.e., legs and hands). However, for some surgical sites involving complex anatomic regions (i.e., head & neck, axilla, abdomen) the lack of depth and size information provided by simple nonimaging probes can reduce the efficacy of surgical guidance with gamma-ray probes. For example, lymphatic drainage patterns can in some areas of the body be quite complex, and often vary widely from patient to patient.

Some investigators have used small gamma cameras instead of nonimaging probe detector heads. This approach works well for a limited number of scenarios in which, for example, the location of a primary lesion is already specified but the margins are not clear, as in osteoid osteoma.

Unlike primary cancer imaging, in cases where metastatic disease is suspected the surgeon generally does not know a priori where the lesions are located. Because of this uncertainty, what may be an acceptable field-of-view for one patient's procedure may not be acceptable for the next patient. As a result, no standard camera size can be specified for all surgeries. Because camera field-of-view is related to the overall physical size of the camera, a large field-of-view camera may be too heavy for surgeons to manipulate, or may hinder access to lesions of interest in the close confines often encountered in surgery. Conversely, a small field-of-view camera, while more maneuverable, may not provide information as to the entire extent and location of the lesion.

Additionally, when the camera is moved from one area of interest to another, or from one angular position to another, information from the earliest position is generally not integrated with information from subsequent positions. Also, information concerning the angulation of the camera with respect to the area of interest generally is not recorded. As a result, it is difficult to ascertain the depth of a lesion located in a particular area of interest. In such cases, the camera also does not provide sufficient information to perform a tomographic backprojection or reconstruction, or to obtain a three dimensional image of the lesion.

SUMMARY OF INVENTION

In one embodiment, the present invention contemplates a tomographic imaging system comprising a moveable detector that is capable of detecting gamma radiation; a position sensor for determining the position and angulation of the detector in relation to a gamma ray emitting source; and a computational device for integrating the position and angulation of the detector with information as to the energy and distribution of gamma rays detected by the detector and deriving a three dimensional representation of the source based on the integration.

The present invention also contemplates a tomographic imaging system comprising a moveable detector that is capable of detecting radiation; a position sensor for determining the position and angulation of the detector in relation to a radiation emitting source; and a computational device for integrating the position and angulation of the detector with information as to the energy and distribution of radiation detected by the detector and deriving a three dimensional representation of the source based on the integration.

The present invention also contemplates a tomographic imaging system comprising a moveable means for detecting radiation; a means for determining the position and angulation of the detector means in relation to a radiation emitting source; and a means for integrating the position and angulation of the detector means with information as to the energy and distribution of radiation detected by the detector means and deriving a three dimensional representation of the source based on the integration.

The present invention also contemplates a method of imaging a radiation emitting lesion located in a volume of interest comprising the steps of positioning a detector that is sensitive to radiation at multiple locations in relation to the lesion to obtain information as to the energy and distribution of the radiation detected by the detector; recording the positions and angulations of the detector in relation to the lesion; integrating the positions and angulations of the detector with the energy and distribution information; and deriving a three dimensional representation of the lesion based on the integration.

The present invention also contemplates a method of imaging a gamma ray emitting lesion in a patient comprising the steps of positioning a gamma camera that is sensitive to gamma radiation at multiple locations in relation to the lesion to obtain information as to the energy and distribution of gamma rays detected by the detector; recording the positions and angulations of the camera in relation to the lesion; integrating the positions and angulations of the camera with the energy and distribution information; and deriving a three dimensional representation of the lesion based on the integration.

The present invention also contemplates a method of radioactive waste surveillance comprising the steps of positioning a detector at multiple locations in relation to the waste, the detector being sensitive to radiation emitted by the waste and providing information as to the energy and distribution of the radiation detected by the detector; recording the positions and angulations of the detector in relation to the waste; integrating the positions and angulations of the detector with the source and distribution information; and deriving a three dimensional representation of the waste based on the integration.

BRIEF DESCRIPTION OF THE DRAWINGS

The benefits and advantages of the present invention will become more readily apparent to those of ordinary skill in the relevant art after reviewing the following detailed description and accompanying drawings, wherein.

DETAILED DESCRIPTION OF THE INVENTION

Figure 1:
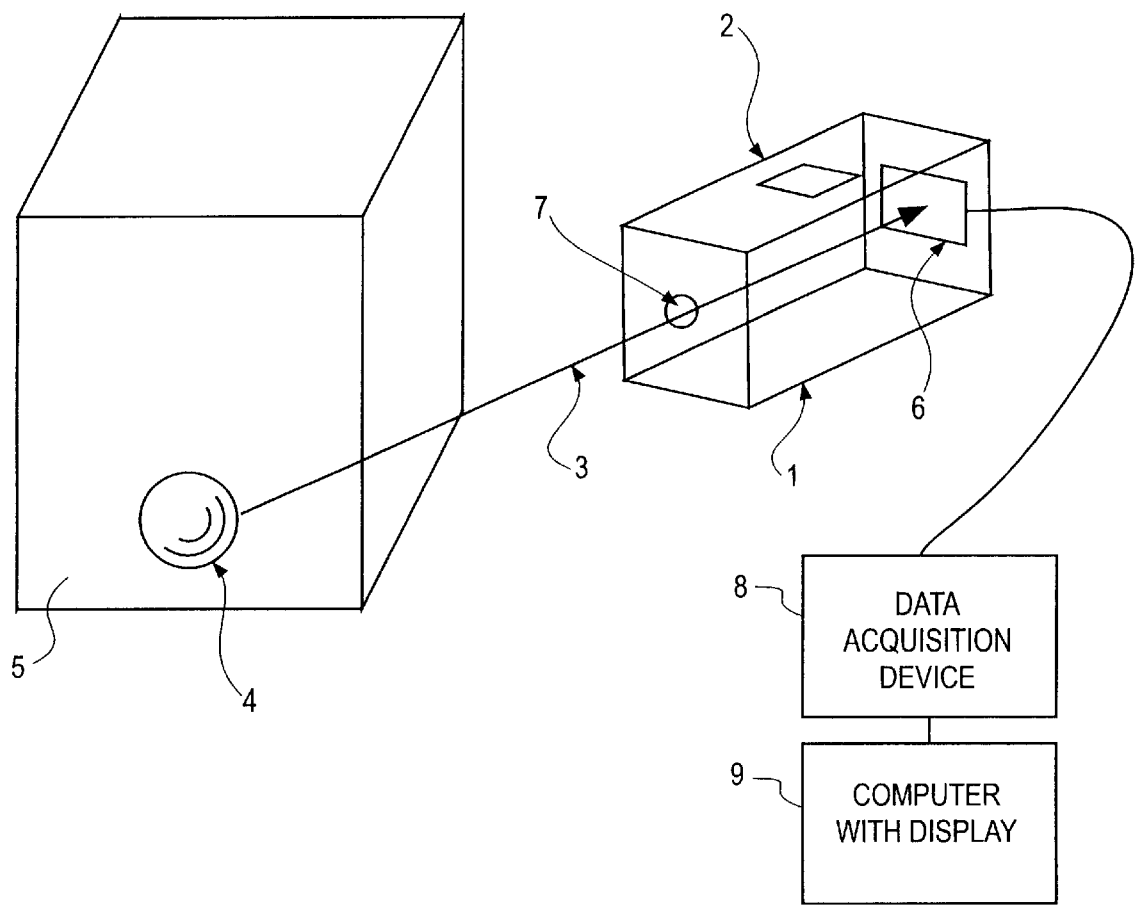
FIG. 1 shows a schematic of the inventive imaging system using a single hand-held pinhole gamma camera.

Referring now to FIG. 1, it is seen that in one embodiment of the inventive imaging system, a moveable detector 1 that is sensitive to radiation 3 emitted by a source 4 in a volume of interest 5 is provided.

In a preferred embodiment, the detector can be a hand held gamma camera that provides a two dimensional image of radiation that enters the camera through an aperture 7 and strikes material on a backplane 6, which material is sensitive to the deposition of energy from incident gamma rays.

Figure 3:
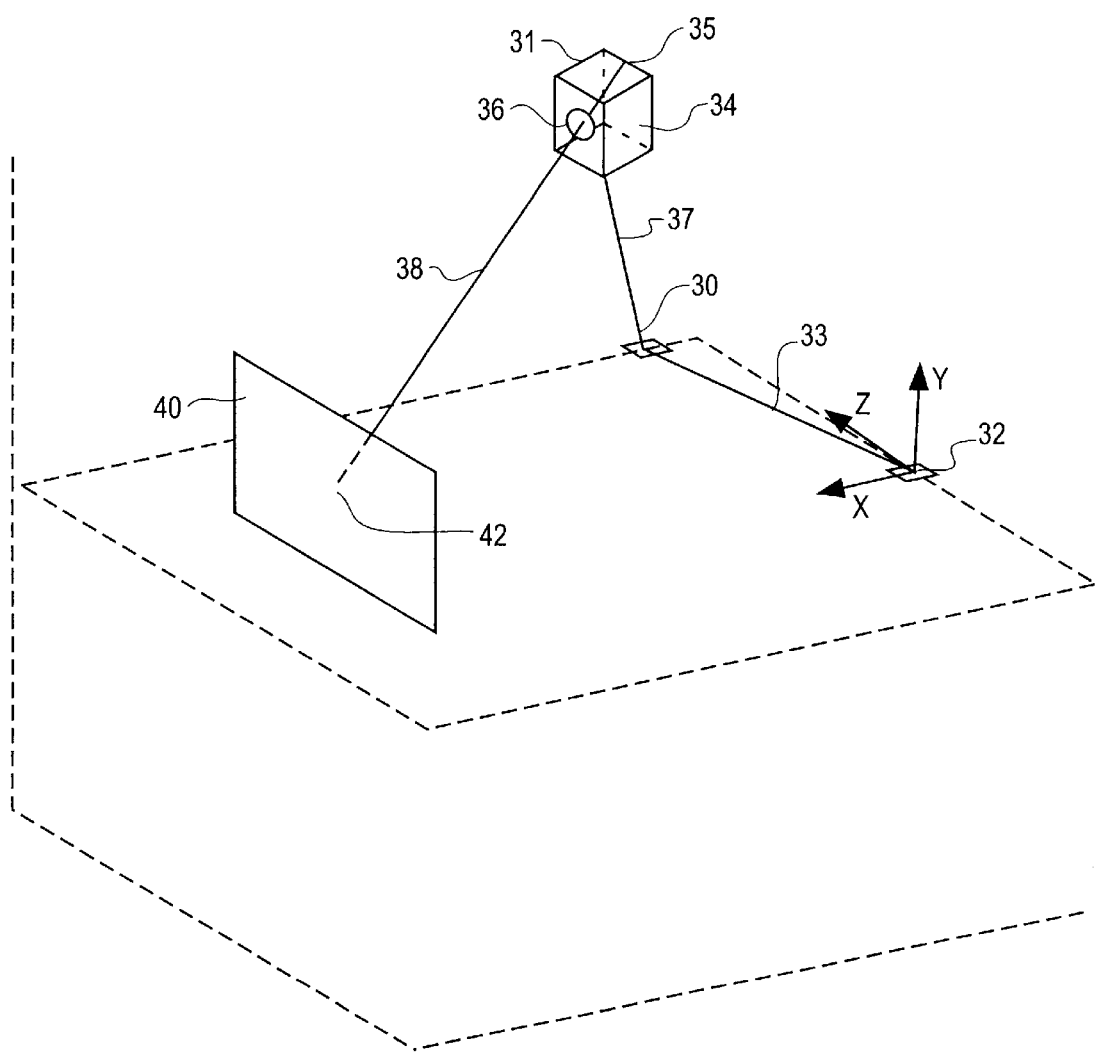
FIG. 3 shows an example of a graphic user interface supplying a user with feedback about the location of a hand-held pinhole gamma camera.

Affixed rigidly to the camera body is a position sensor 2, or some other device for recording the position and angulation of the camera in time with respect to the source 4 and volume of interest 5. Information regarding the camera's position and angulation, and the detected radiation are transmitted to a data acquisition device 8 and sent digitally to a computer 9 or other computational device with a display also sometimes referred to as a graphical user interface (an example of which is shown in FIG. 3).

The camera 1 may contain shielding material to reduce the number of events detected on the backplane that do not traverse the aperture. The aperture may be a single hole (i.e, "pinhole") or multiple pinholes ("i.e., coded aperture"), or many pinholes in a grid ("parallel hole collimator"). The pinhole grid pattern may converge ("converging hole collimator"), diverge ("diverging hole collimator"), or slant ("slant hole collimator").

In one embodiment, a one-inch square field-of-view portable gamma camera was built, using a Hamamatsu R5900 C8 position-sensitive photomultiplier. The camera head weighed less than two pounds, and included a tungsten housing and pinhole assembly. A pinhole size of 2.5 mm diameter was selected to provide good spatial resolution. A GSO ($Gd_2SiO_5$) crystal array (2 mm pitch) was affixed to the photomultiplier face.

The camera head is placed on a plastic handle in which a Polhemus electromagnetic position sensor is disposed. The Polhemus system includes an electromagnetic transmitter and one or more receivers. The receiver is about one cubic centimeter in size. The Polhemus transmitter and the camera are attached via cables to an electronics controller assembly, which includes analog-to-digital conversion and power circuitry. The Polhemus circuitry interfaces with the computer via a serial port, using ASCII commands that are interpreted by the controller circuitry. The Polhemus Euler angle specification system is similar to the standard "Goldstein" type angles.

The inventive imaging system and method integrates information as to the energy and distribution of gamma rays detected by the detector backplane 6 as well as the position and angulation of the detector backplane 6 in time. Integrating positions and angulations of the detector backplane with source information solves several problems. For example, the angulation information provided by the imaging system is needed to perform a tomographic backprojection or reconstruction with the data generated from the detector. The angulation information also is needed to determine the depth of a source or lesion. Further, data is not discarded when the detector is moved to different positions and angulations and the field of view of the hand-held camera is determined by the position of the camera in relation to the lesion of interest, so that the size of the camera is not a critical determinant of the field-of-view. A small camera that can fit in close quarters can be moved by the user to provide information relating to a much large field-of-view.

Figure 2A:
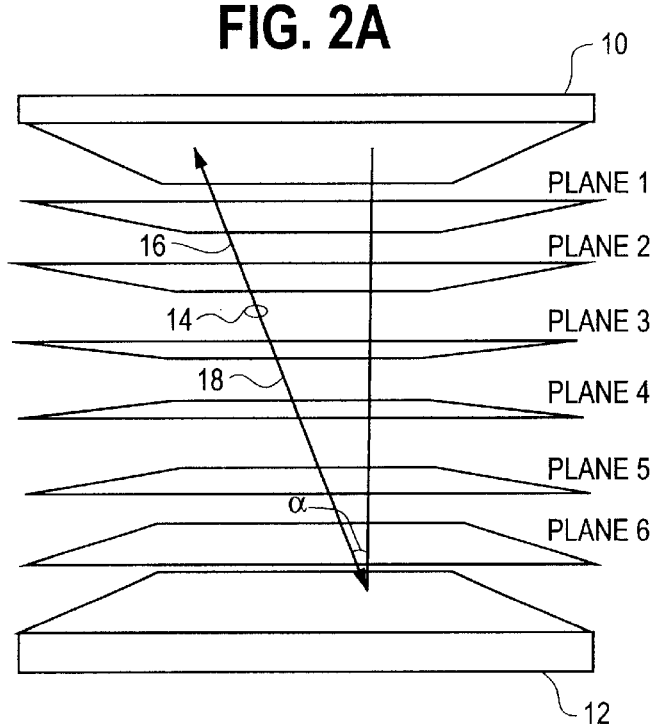
FIG. 2 shows a comparison of the geometry for positron emission mammography backprojection and hand-held pinhole gamma camera backprojection.
Figure 2B:
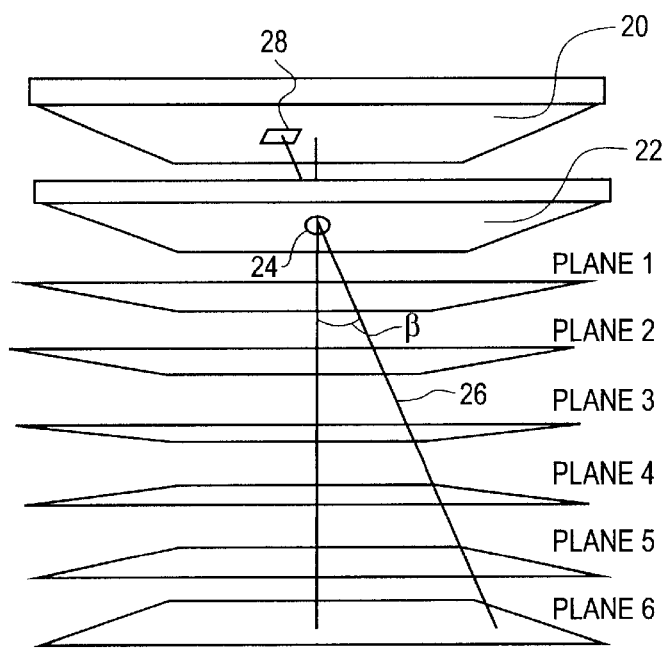

Referring now to FIGS. 2A and 2B, it is seen that a "backprojection method", can be used to determine the position of the source and to provide a three dimensional mapping or representation of the source, which for example can be a lesion in a patient that has been injected with a gamma ray emitting radiotracer. In a backprojection, a line is drawn (or calculated) from the detector in which energy was deposited, back towards the location where the gamma ray could have originated.

Referring now to FIG. 2A, it is seen that in a typical positron emission mammography geometry, a positron annihilation 14 results in rays 16 and 18 from coincident events detected on two parallel detector planes 10 and 12, which are projected onto virtual planes (plane 1–plane 6) between the two detectors. Pixel values are incremented at the locations on each virtual plane intersected by the rays. A coincident angle α is defined by the angle of incidence of the ray 18 on the detector plane 12.

An example of a hand-held camera backprojection is shown in FIG. 2B. In a typical sequence of data and image processing as shown in FIG. 2B, each event recorded by the detector 20, which includes a scintillator in an array mounted on a position-sensitive photomultiplier, or 'PMT', is assigned to a particular crystal in the detector array, hereafter sometimes referred to as the "event origin". Both the location of the event origin 28 and the location of the center of the pinhole 24 are dependent on the position and angulation of the receiver. Because the pinhole, detector array, and position sensor are all on a single rigid body, the Euler angle formalism allows transformation from the rotating and translating camera frame of reference to the stationary frame of reference as for example is described in Goldstein, Classical Mechanics, Addison-Wesley Publishing Co., Copyright 1950, pages 107–109. An algorithm implemented in a computer program utilizes the angular and position information for each detected event to calculate the location of the event origin and center of the pinhole in the stationary frame of reference.

As shown in FIG. 2B, ray 26 originating at event origin 28 is projected from the detector plane 20 through the center of a pinhole 24 disposed on plane 22 and onto a set of stationary virtual planes (plane 1–plane 6). Again, pixel values are incremented at the locations on each stationary virtual plane intersected by the rays. In the hand-held case, unlike in typical positron emission mammography as for example is shown in FIG. 2A, the detector plane 20 is free to move with respect to the stationary virtual planes. The output of the Polhemus receiver that is attached to the hand-held camera can be used to determine the ray angle β.

Referring now to FIG. 3 it is seen that a graphical user interface supplies a user with a virtual image of the handheld camera 31, Polhemus transmitter 32 and a plane 40 in the backprojection volume. A line 33 is drawn between the Polhemus transmitter 32 to the Polhemus receiver 30, which is located at the base of the hand-held camera 31. Although the origin of the stationary frame of reference can be placed in many different locations, for clarity we are placing it at the location of the Polhemus transmitter in FIG. 3. A virtual ray 38 is generated arising from the event origin 35, where the energy of the gamma ray was deposited in the backplane 34 of the camera 31. A second line 37 shows the location of the rigid body hand held camera with respect to the Polhemus receiver 30. The direction of the virtual ray is determined using the two point formula for a line. These two points (in the stationary reference frame) include the event location 35, and the center of the pinhole 36.

The virtual ray 38 is allowed to project onto one or more virtual planes, for example plane 40. At every point on each virtual plane that the virtual ray intersects (e.g., 42 in FIG. 3), the virtual plane's pixel value is incremented by one. In an alternative embodiment the pixel value may be incremented by a number different from one (e.g., in excess of one) and may factor in such weighting factors as efficiency and dwell time.

In FIGS. 2B and 3, the virtual planes (Planes 1–6 in FIG. 2B) or plane (40 in FIG. 3) are set at varying distances X from the origin of the stationary frame of reference. The origin of the state of reference is shown as 32 in FIG. 3, which in this figure is also the location of the Polhemus transmitter. Typically a physician performing a biopsy will select one coordinate to be referred to as depth, and in this case "X" is the coordinate associated with the depth. In an alternative embodiment, Y or Z can be the coordinates designated for depth. Position sensing can be implemented by utilizing a transmitter (set at the origin of the stationary frame of reference 32 in FIG. 3) that creates an electromagnetic field, and one or more receivers (31 in FIG. 3) that send information about the strength and direction of the electromagnetic field in order to tell the computer where the receiver is located. Alternatively, position sensing can be implemented with optical detectors or with potentiometers.

The depth information presented by this backprojection method is similar to a tomographic image in which a structure appears sharpest in the plane in which the structure is located. The positron emission mammography backprojection method reproduces this behavior, since if a source is actually present at the location along X of a particular virtual plane, rays passing through the source will converge in the same source virtual plane and form a sharp, bright point there. For positron emission mammography, the intersection of source rays form a blur in virtual planes far from the point source's plane, and are sharpest and brightest in the source's actual plane.

The behavior of a moving handheld camera in the present invention is different from the typical behavior of a stationary gamma camera. If the handheld camera were stationary during the entire data acquisition, rays from a source would form a disk on each virtual plane, with the size of the disk depending on the distance to the detector plane of the pinhole camera. This stationary handheld camera is equivalent to a simple stationary pinhole camera projection image, and would not provide any depth information.

However, when the handheld camera is moved, the motion of the handheld camera causes a blurring in each virtual plane that does not actually contain the source. In the actual source plane, rays still converge to a point. Backprojecting from a moving pinhole camera thus has the salutary effect of distinguishing overlapping sources from one another as is shown in FIGS. 4A–4C.

Figure 4A:
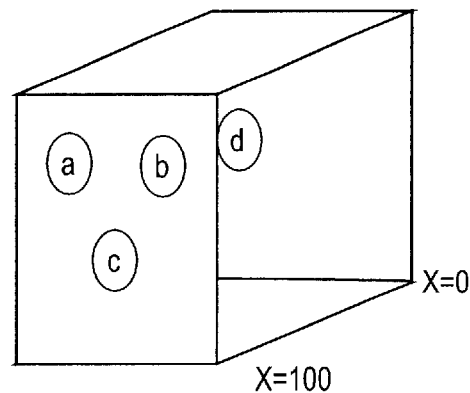
FIG. 4 illustrates a comparison of simulated backprojection images derived from a hand-held pinhole gamma camera.
FIG. 4B is inverted with respect to FIG. 4C.

FIG. 4A depicts simulation conditions in which three coplanar sources (a,b,c) are placed in plane X=100, and one source (d) is placed in plane X=0.

Figure 4B:
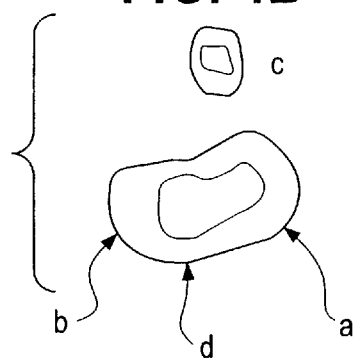

FIG. 4B depicts an image as seen by a pinhole camera when no camera motion occurs. The sources appear inverted because of pinhole geometry. All four sources (a,b,c,d) contribute to the image. Because of overlap from source d, images of sources a and b cannot be individually resolved.

Figure 4C:
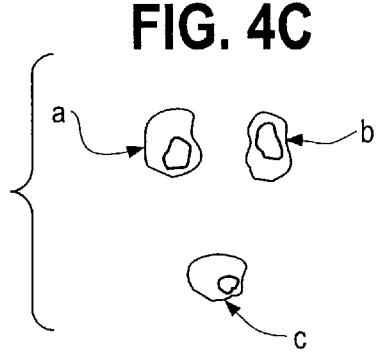

FIG. 4C shows a backprojected image at plane X=100 obtained with a simulation of a moving pinhole camera. FIG. 4C is not inverted because the software has corrected for inversion in order to present more intuitive information to the surgeon using the moving pinhole camera. In FIG. 4C, backprojection removes the image of source d (at X=0) from the images of coplanar sources a, b, c.

Because the hand-held camera by definition has no predetermined orbit, the efficiency of data collection must be calculated for each actual position and angle in the orbit. The implemented efficiency correction involves backprojecting onto virtual planes the influence of all possible events that could have been detected on the detector plane for the time that the handheld detector was in each particular position. The actual event backprojection is then divided by this efficiency backprojection to get an efficiency-corrected backprojection data set. An approximate efficiency correction for the hand-held detector was developed by calculating a simulated efficiency backprojection that was dependent on the positions and angulations encountered along the hand-held camera's orbit. This efficiency correction is shown schematically in FIGS. 5A and 5B.

Figure 5A:
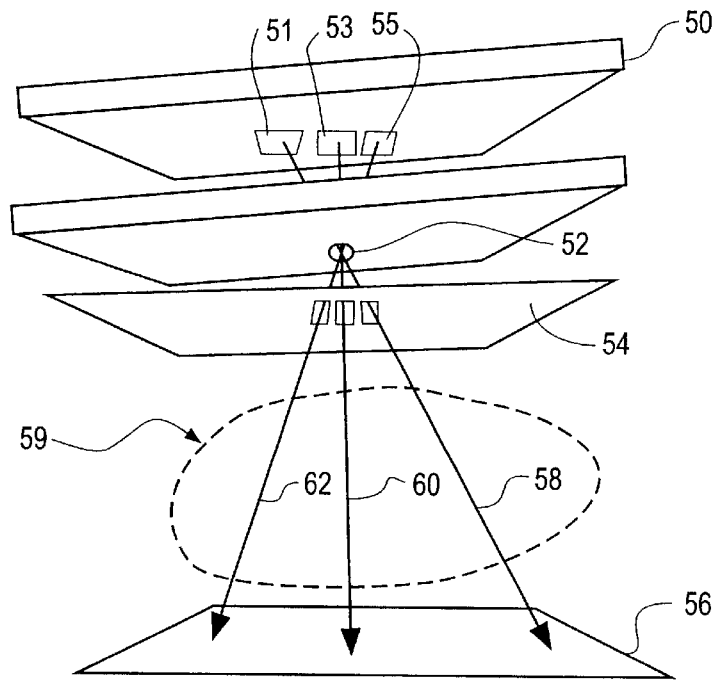
FIG. 5 illustrates an efficiency correction calculation for a hand-held pinhole gamma camera.
Figure 5B:
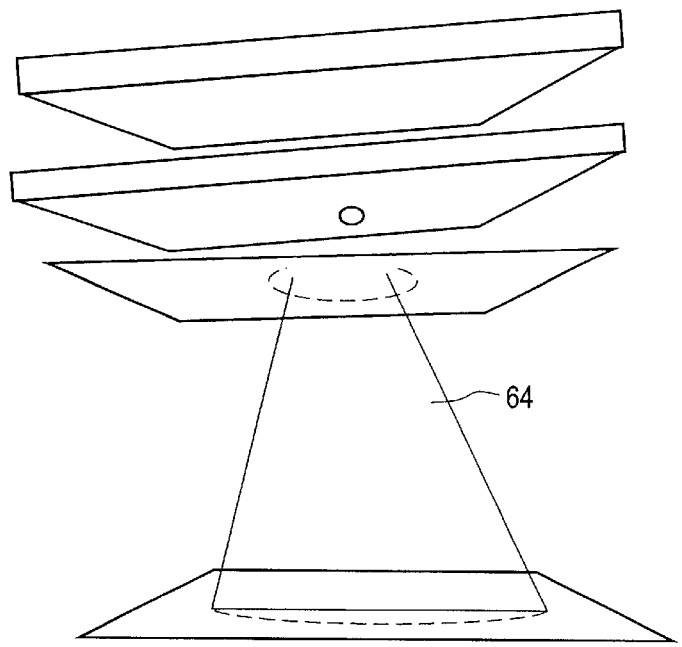

Referring now to FIGS. 5A and 5B, it is seen that a first-order correction for inhomogeneity in efficiency has been implemented, by calculating the efficiency of the acquisition orbit in collecting counts from a simulated uniformly distributed source filling the specified volume of interest. For each simulated event with position and angulation encountered per unit time by the hand-held camera's orbit, each element of the detector backplane projects a ray through a pinhole.

FIG. 5A shows an example of three detector elements 51, 53 and 55 disposed on moving detector backplane 50 contributing projections 58, 60 and 62, which pass through moving pinhole 52. A mathematical artifice is employed to ensure that only the set of virtual rays traversing the volume of interest 59 will enter into the image formation process. The artifice includes drawing the boundaries 54 and 56 of the volume of interest 59, backprojecting the virtual rays 58, 60 and 62 through the volume of interest 59, and determining mathematically where the virtual rays cross the boundaries of the volume of interest. The two locations on the boundaries 54 and 56 of the volume of interest 59 are then considered to have generated new lines. These new lines can be considered to be like the lines of response generated by coincident events in a positron emission tomography ("PET") scanner. These are called "pseudo-coincident" events.

FIG. 5B shows an illustration of multiple simulated projections on boundary planes and reconstruction volume. It is seen that the accumulated pseudo-coincident events from all rays that intersect the boundary planes on both sides of the reconstruction volume 64 are binned into a sinogram, just as would be the case in a PET scanner. Because the orbit of the hand-held camera is not fixed, it is necessary to correct the sinogram for the effect of variations in collection efficiency along the orbit. This can be done as follows: the efficiency of the collection of radiation by the hand-held camera is estimated by simulating events in the volume of interest numerically (e.g., through Monte-Carlo statistical methods, or through analytic approaches), and using a computer to calculate the events that would have been detected by the hand-held camera as the camera ran through the actual orbit of the hand-held camera around the volume of interest. This numerical result yields an efficiency sinogram. The sinogram from actual gamma-ray events can be divided by the efficiency sinogram before proceeding to backprojection or reconstruction. The same correction strategy follows for multiple camera heads as well, in which simulations of events arising in the volume of interest are combined with the known orbit of the camera in order to obtain an efficiency correction sinogram or other correction factor or matrix. The simulations can be updated as the camera moves to different positions.

Figure 6A:
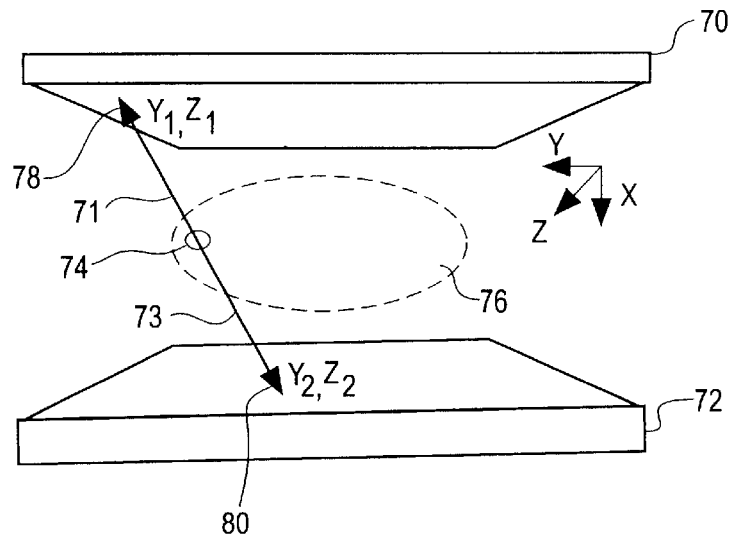
FIG. 6 compares positron emission mammography reconstruction geometry and hand-held pinhole gamma camera backprojection geometry.
Figure 6B:
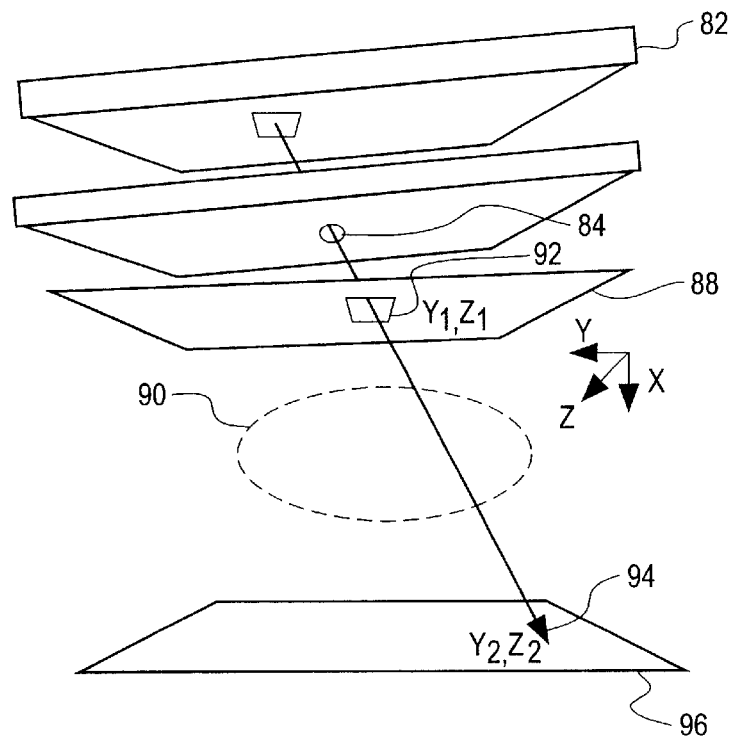

As shown in FIGS. 6A and 6B, it is possible to cast the handheld pinhole camera configuration (FIG. 6B) into a geometry that is similar to positron emission mammography (FIG. 6A). This is accomplished by representing the boundaries of the volume of reconstruction prescribed by the user as if there were detectors at these boundary locations.

FIG. 6A shows geometry for reconstruction of positron emission mammography data sets. A positron annihilation 74 results in coincident gamma rays 71 and 73 that are detected at coordinates (Y1,Z1) on detector 70 and at coordinates (Y2,Z2) on detector 72. A reconstruction volume 76 is defined between the two detector planes 70 and 72. A sinogram of pixels on the two detector planes is submitted for reconstruction by an iterative Monte Carlo algorithm.

FIG. 6B shows a formalism that converts rays from a moving pinhole into the equivalent of the dual detector geometry depicted in FIG. 6A. Boundary planes 88 and 96 are defined, which are traversed by rays passing through the pinhole 84. The detector backplane 82 is beyond the volume of reconstruction. The event origin on the detector backplane 82 is backprojected onto the boundary 88 of the reconstruction volume 90. The location of intersection 92 with this boundary 88 is then treated as if the ray actually arose from this location 92 on the boundary volume. Thus even though the physical locations of the detectors are beyond the boundaries of the volume of reconstruction, the event data is treated as if it was from lines which originated and terminated in "virtual" detectors 88 and 96 placed at the boundary locations 92 and 94.

The pixels on the boundary planes 88 and 96 that are struck by backprojected rays are considered to arise from two "pseudo-coincident" events. The event can be considered to be equivalent to coincident gamma rays detected at coordinates (Y1,Z1) on planar detector 88 and coordinates (Y2,Z2) on planar detector 96. A sinogram is then formed from coincident events in these planar or "pseudo" detectors 88 and 96, and the sinogram is reconstructed as in the positron emission mammography case.

Creating virtual detectors on the boundary planes, which fit the handheld camera data into a positron emission mammography-like geometry (as in FIG. 2), results in a loss of some angular information, because rays that do not hit both of the virtual boundary planes are discarded. In an alternative embodiment, it is possible to use boundary surfaces of other shapes and locations than parallel planes to reduce the amount of angular information that is lost. For example, the boundary surfaces could form a six-sided cube enclosing the reconstruction volume.

Figure 7:
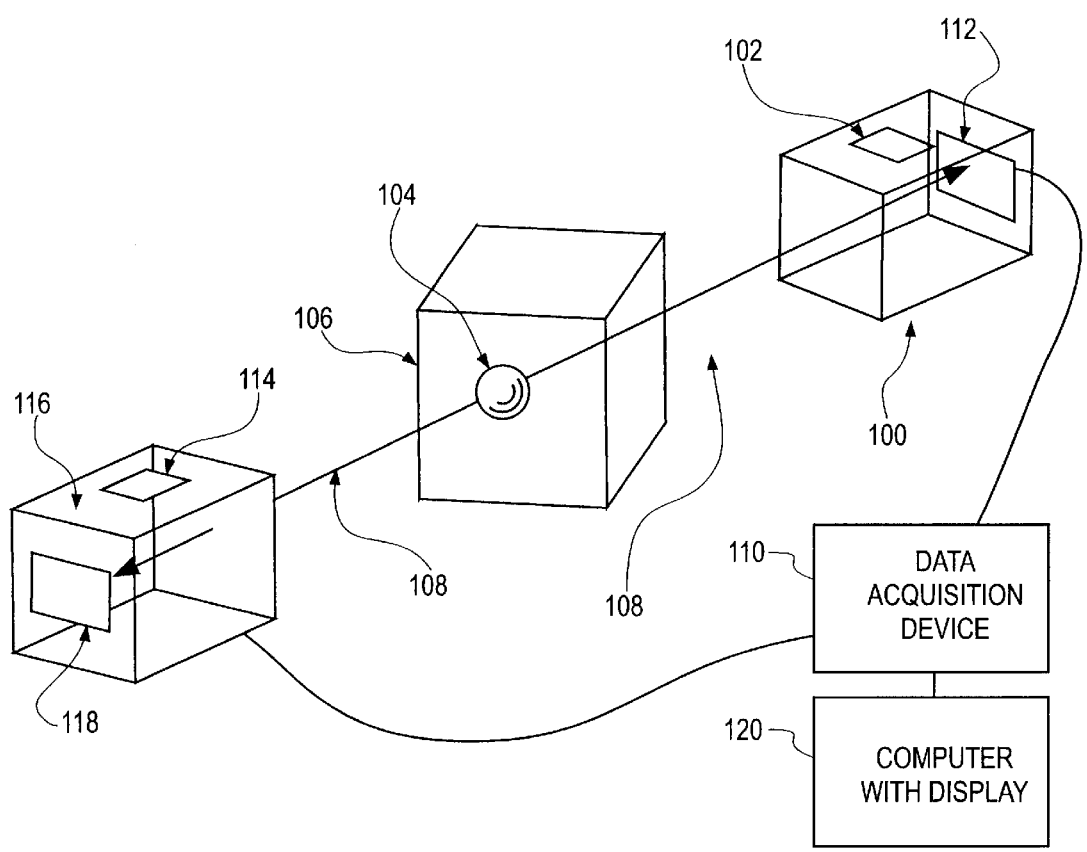
FIG. 7 illustrates an alternative embodiment of the imaging system using a multiple gammaray sensitive cameras to define a line of backprojection between two of the cameras.

FIG. 7 shows an alternative embodiment where multiple detectors 100 and 116 are used. For example, both detectors can be handheld gamma cameras sensitive to radiation of 511 keV energy emitted coincidently by positron annihilation. Alternatively, each gamma camera could be sensitive to prompt radiation emitted in two directions by Indium-111. Alternatively, one of the detectors can be a handheld gamma camera and the other detector can be a stationary detector.

A positron annihilation occurring in source 104 within a volume of interest 106 emits coincident radiation 108 that is deposited simultaneously in two gamma-ray detectors at positions 112 and 118. Volume of interest 106 can be prescribed by the user of the system, or can be defined on the basis of other mathematical reasons. Position sensors 102 and 114 are affixed to the respective detectors 100 and 116. The detectors 100 and 116 are connected to a data acquisition device 110 and a computer 120 with display. The data acquisition device 110 gets input from both cameras as well as from position sensors 102 and 114 mounted on both cameras, and can determine whether coincidence occurred in hardware (via an AND gate) or software (by inspection of a time-stamped list mode file) or both.

Where one gamma camera and one stationary detector are used, the position-sensing receiver can be affixed to the hand-held component alone. In that case, since the other detector component(s) would not move, the position of these detector components can be determined through a rigid-body relationship to the Polhemus transmitter or other position-sensing apparatus.

When the lines from many energy depositions are accumulated, they generally cross at the location of the actual source (backprojection). This process can be modeled numerically as in FIG. 2B, in which a set of virtual planes are imagined, and every time a plane is struck by a back-projected line, the pixel on the plane which is struck is incremented by a value. The net effect is that in the planes that contain the actual source object (i.e., source plane), the pixel at the source's location in that plane has a high value.

It also is possible to simultaneously detect "prompt" coincidences in the two detector heads rather than annihilation coincidences, to reduce the effect of background radiation. For annihilation coincidences, gamma rays are formed from the annihilation of positions and electrons, while for prompt coincidences gamma rays are emitted essentially simultaneously but are not approximately 180 degrees apart as for annihilation radiation.

Figure 8:
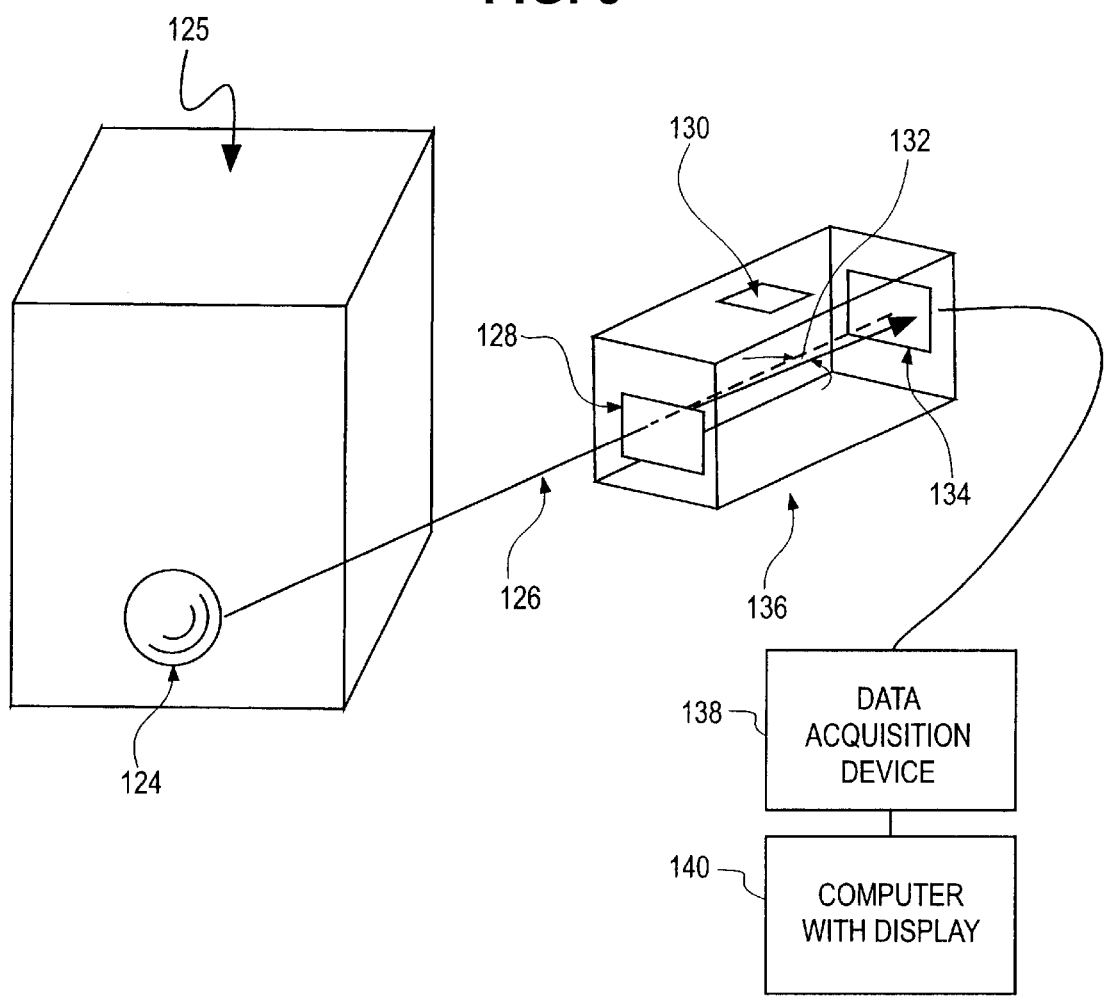
FIG. 8 illustrates an alternative embodiment utilizing a Compton scattering approach to define a line of backprojection.

Referring now to FIG. 8, it is seen that a "Compton camera" alternatively can be used to detect radiation from a source 124. A gamma ray 126 is emitted by a source 124 located in a volume of interest 125. Energy from the gamma ray 126 is deposited into a first detector plane 128 and then into a second detector plane 134 of a Compton camera 136 with position sensor 130, taking into account angular deviation 132 due to Compton interaction. Also included in the system are a data acquisition device 138 and a computer 140 with display. As in the case of the pinhole camera (FIG. 1), a set of virtual rays can be generated for each event which deposits energy in both detector planes and each of these virtual rays can be backprojected to derive an image of the source 124.

Alternatively, the camera can be a mobile nonimaging detector or probe that records the amount of radiation detected at each point in time. The term "camera" is used loosely in reference to a nonimaging detector, because no image is formed at the backplane. In the case of a nonimaging detector, the number of counts received by the backplane can be integrated with the position and angulation data to backproject rays into a volume, thereby creating an image of the source. The backprojection method is similar to the method shown in FIG. 2B and subsequent figures, except that the "event location" 28 of FIG. 2B is the location of the detector element of the nonimaging detector, rather than a single pixel on a detector plane as represented in FIG. 2B.

Alternatively, one component of the camera may emit radiation that passes through an area of interest and is then recorded by another component of the detector.

Alternatively it is possible to register data from anatomic imaging modalities such as ultrasound or magnetic resonance imaging to demonstrate needle tips or other landmarks of interest. The registration can be accomplished using position sensors that are touched by the user to fiduciary markers visible in the anatomic imaging modality or to the naked eye, and having these position sensors relay information to the computer that is displaying the images derived from data generated by the handheld scanner.

Using the principles of the invention as discussed herein, it is possible for the single camera head embodiments of FIGS. 1 and 8 to be placed within a body cavity or to be used intraoperatively.

Figure 9:
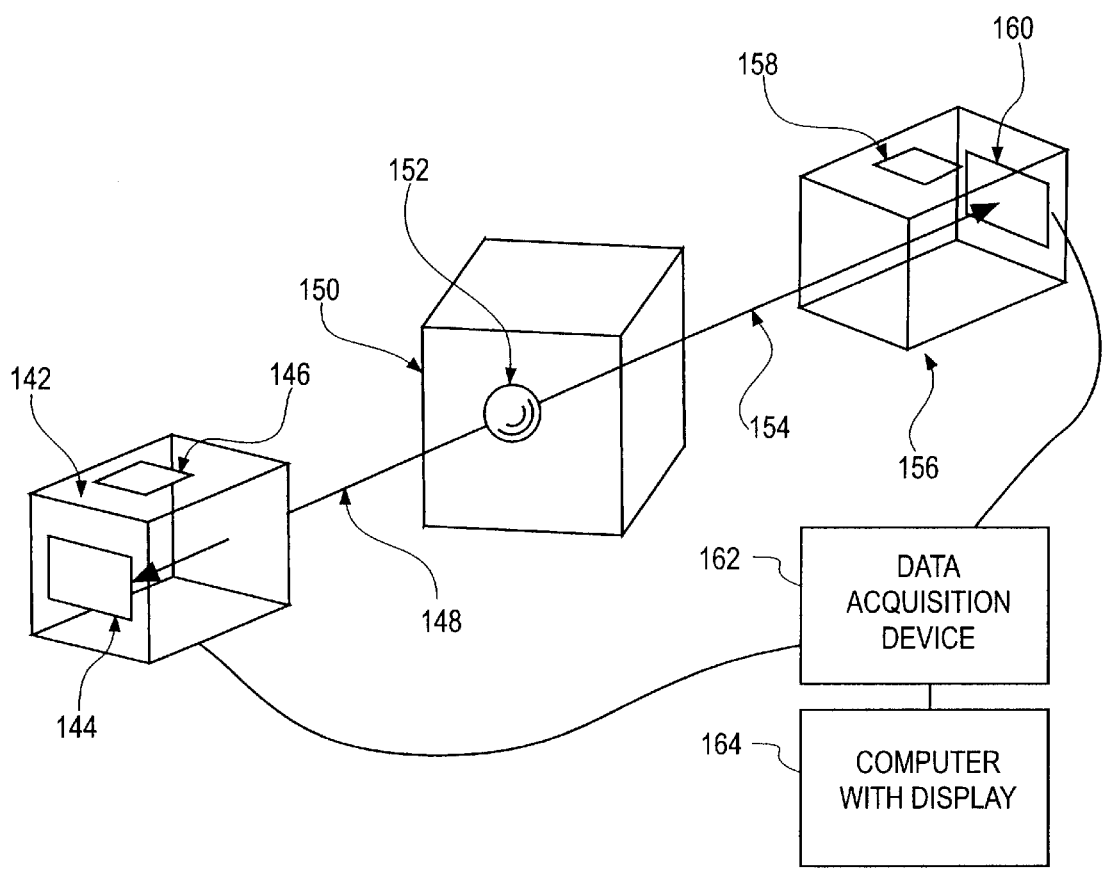
FIG. 9 illustrates an alternative embodiment of the imaging system using a multiple cameras to define a line of backprojection, in which the cameras are of different sizes.

It also is possible for one of the two gamma camera heads shown in FIG. 7 to be miniaturized so that one or many of the camera heads can be in a body cavity and other camera heads be outside the body cavity, or for all camera heads to be inside the body cavity. For example, one of the camera heads of FIG. 7 can be small, and can be inserted via a rectal probe to examine a patient's prostate, while the second detector head of FIG. 7 can be larger and can be placed anterior to the patient's pelvis. An example of such an asymmetric configuration is illustrated in FIG. 9. Referring now to FIG. 9, it is seen that a first camera 156, which can inserted into a body cavity or orifice, includes a position sensor 158 and a backplane 160. A second camera 142 is disposed outside the patient's body. The second camera includes a second position sensor 146 and a second backplane 144. The cameras are connected to a data acquisition device 162 and a computer 164 with a display. A gamma-ray emitting source 152 is located in a volume of interest 150 between the two cameras. The cameras detect emitted coincident or prompt gamma rays 148 and 154.

Figure 10:
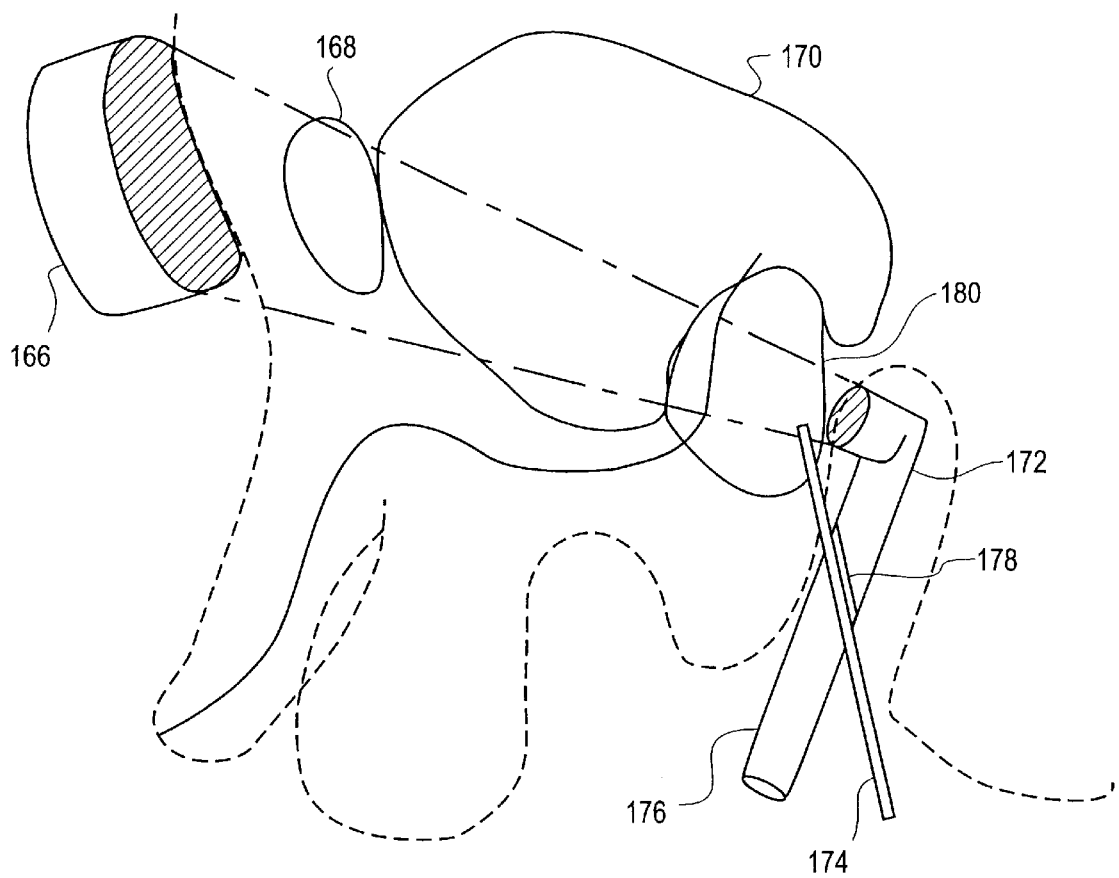
FIG. 10 illustrates an alternative embodiment in which two gamma-ray sensitive cameras can obtain an image of the prostate.

FIG. 10 illustrates the use of the camera arrangement of FIG. 9 to obtain an image of the prostate. Referring now to FIG. 10, it is seen that a first camera 166 is disposed anterior to the urinary bladder 170 and pubic symphysis 168. A second smaller camera 172 is disposed inside the rectal vault near the prostate 180. In some cases it may be preferable to decrease the amount of background activity detected by the camera by, for example, draining the bladder with a catheter inserted through the urethra. The second camera 172 includes a handle 176 with an aperture 178 through which an optional biopsy or intervention needle 174 can be inserted. The needle, which is thus rigidly attached to camera 172, can be used to help the user localize objects of interest in space. By using rigid-body mechanics it is possible to display a "virtual needle tip" in the same graphical user interface that is showing the detector positions and the image of the object of interest.

Alternatively, the needle need not be inserted through the handle of one of the detectors and instead can be separate from the detector. In such a case, a position sensor can be attached to the needle or to a holder for the needle.

Alternatively the needle 174 can be replaced by some other form of focal intervention such as for example, a focused ultrasound beam, radiotherapy beam, heating element, or a light guide.

Another way of deriving an image is through reconstruction rather than backprojection. In a backprojection, when the lines cross planes that do not contain the actual source (out-of-source planes), pixels on the planes are incremented. This has the effect of making it appear that background activity is present in the out-of-source planes (i.e., that do not actually contain a source). This false background activity in each plane from sources in other planes can obscure the effect of true sources in each plane. In a reconstruction, the contributions of backprojected lines from source planes to out-of-source planes are minimized or eliminated. Thus there is less background activity outside the source plane, thereby increasing detectability of sources.

The classic method of performing reconstructions is called filtered backprojection, and is employed in x-ray computed tomography. In this method projection sets are decomposed into Fourier components, which are then modified with frequency-dependent filters. The filtered components are reverse transformed and backprojected.

Because a handheld gamma camera generally does not give a full set of angular information about the source distribution, filtered backprojections are not as useful as they would be for x-ray computed tomography where the detector goes around the source in a complete rotation. Therefore, for limited angle projection sets, which for example are provided by the inventive imaging system when a hand held gamma camera is used, it is preferable to use an iterative reconstruction, which is generally more flexible than a filtered backprojection approach.

Iterative reconstructions take an initial estimate as to the source distribution (i.e., "estimated source distribution"), and perform a projection of this estimate onto the known positions of the detectors. The projection of the estimated source distribution is then compared to the actual projection from the source, and the estimated source distribution is modified based on this comparison. In most cases, assuming that the estimate and the method of modifying the estimated source distribution were reasonable, an estimated source distribution is arrived at that is very close to the actual source distribution.

There are several methods of modifying the estimated source distribution. One such method is the maximum likelihood estimation method ("MLE"), as for example is described in Worstell et al., "Monte Carlo-based Implementation of the ML-EM Algorithm for 3-D PET Reconstruction," Proceedings IEEE Nucl. Sci. Symp. 1998. But other methods also are contemplated.

Another way of representing the process in which the estimated source distribution would cause a particular set of projections is with a matrix. This matrix is typically referred to as a system transfer function, or as a transition matrix The system transfer matrix can be thought of as a method of establishing which detectors would be excited by a source at which location. The system transfer function can be assembled analytically for cameras with detectors at known fixed positions. For rings of detectors, as in conventional PET scanners or SPECT scanner heads with fixed orbits, it is possible to solve for system transfer functions using analytical formulas, and to apply symmetries to reduce the size of the transfer functions (so-called "ordered-subset" methods).

In the case where one or more of the detectors are hand-held, the system transfer function is not readily calculated using analytical formulas, and there are few symmetries that can be used to reduce the matrix size. Accordingly, Monte Carlo methods have been used to determine the system transfer function. Every location at which the detectors have been, represents a set of possible events, and among these possible events a Monte Carlo simulation is used to generate the system transfer function. Alternatively, the set of all possible events can be tabulated at each position in order to generate a system transfer function. Since with a handheld detector the user can vary the dwell time that is spent at each detector location, a dwell time factor also can be incorporated in the system transfer function incrementing the set of possible events at each detector location for the dwell time at that location.

Once a system transfer function is determined, iterative reconstruction methods listed above, or other iterative reconstruction methods, are used to generate estimates for the actual source distribution. For example, in one reconstruction method, a user prescribes a volume of reconstruction, so that events outside this volume are not allowed in the transition matrix. In an alternative reconstruction method, zero elements of the transition matrix are discarded using a "sparse matrix" approach.

Another application for position-integrating technology is in the surveillance of radioactive waste. There is a need for a method to describe the distribution (in three dimensions) of radioactive materials generated by, for example, a nuclear power station. These materials are occasionally buried underground as nuclear waste. High-level radioactive waste has been generated in the form of spent fuel from civilian nuclear power plants in the U.S. The task of cleaning up high-level and low-level radioactive waste has been investigated by the Environment Management program at the Department of Energy, with a Base Case estimate of $227 billion required for cleanup.

Existing tools for surveillance of decommissioned sites include Geiger counters and portable gamma cameras. Robotic devices have been made and rapid response vehicles for radioactive surveillance are also known. It is believed that no existing product provides depth information about radioactive sources. This depth information is important not only in locating the radioactive source for removal, but also in estimating the amount of buried radioactive material.

It is contemplated that methods developed for medical applications can be used for radioactive waste surveillance, provided that the one-inch diameter gamma camera for surgical applications is replaced with a larger (e.g., 10-inch diameter) gamma camera, and the sensor (e.g., a 1-cm Polhemus electromagnetic sensor) is replaced with one or more Global Position Sensing detectors.

It is contemplated that detectors that are sensitive to radioactive emissions other than gamma-rays also can be used. For example a gamma ray detector array can be replaced with a neutron detector such as a lutetium orthosilicate, which has a high stopping power for neutrons, and the tungsten pinhole face replaced or augmented with cadmium. Through the above extension to neutron radiation, it can be seen that the detector system of this invention can detect many forms of radiation, including gamma radiation, particulate radiation (e.g., neutrons, alpha particles) or electromagnetic radiation.

In the present disclosure, the words "a" or "an" are to be taken to include both the singular and the plural. Conversely, any reference to plural items shall, where appropriate, include the singular.

In the present disclosure, the word "handheld" is to be taken to include any method of moving a part without a fixed predetermined orbit. Thus the use of a human hand to move the part is not required, and computer-directed or servo-controlled positioning is also intended to be covered by the invention disclosure, so long as the orbit is determined according to (or influenced by) the specific requirements determined at the time of examination.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

What is claimed is:

1. A tomographic imaging system comprising:
   a moveable detector that is capable of detecting gamma radiation from a gamma ray emitting source;
   a first position sensor for determining a position and an angulation of the detector in relation to the gamma ray emitting source and a volume of interest, the volume of interest being modifiable by a user; and
   a computational device for integrating the position and angulation of the detector with information as to an energy and a spatial distribution of gamma rays detected by the detector and deriving a three dimensional representation of the gamma ray emitting source based on the integration.

2. The system of claim 1 further comprising a graphical user interface for displaying the three dimensional representation.

3. The system of claim 2 further comprising a needle with a second position sensor affixed thereto, the second position sensor capable of generating a virtual needle tip that can be displayed on the graphic user interface.

4. The system of claim 1, wherein the detector is a gamma camera.

5. The system of claim 1, wherein the detector includes shielding material.

6. The system of claim 5, wherein the shielding material is interrupted by a pinhole, to form a pinhole collimator.

7. The system of claim 5, wherein the shielding material is interrupted by a set of pinholes, to form a coded-aperture collimator.

8. The system of claim 5, wherein the shielding material is interrupted by a set of pinholes configured to form a parallel hole collimator.

9. The system of claim 5, wherein the shielding material is interrupted by a set of pinholes configured to form a converging hole collimator.

10. The system of claim 5, wherein the shielding material is interrupted by a set of pinholes configured to form a diverging hole collimator.

11. The system of claim 5, wherein the shielding material is interrupted by a set of pinholes configured to form a slant hole collimator.

12. The system of claim 1, further comprising a second detector that is capable of detecting gamma radiation, and a second position sensor that is configured to determine a position and an angulation of the second detector in relation to the volume of interest.

13. The system of claim 12, wherein the computational device is further configured to integrate information as to an energy and a spatial distribution of gamma rays detected by the second detector with the position and angulation of the second detector.

14. The system of claim 12, further comprising a data acquisition apparatus for determining whether the detectors are struck by the gamma rays coincidently.

15. The system of claim 12, wherein one or more of the detectors is configured to be disposed in a body cavity.

16. The system of claim 12 further comprising a needle inserted through an aperture in one of the detectors, the needle providing a virtual needle tip that can be displayed on a graphic user interface.

17. The system of claim 1, wherein the detector is a Compton camera.

18. A tomographic imaging system comprising:
 a moveable detector that is capable of detecting radiation from a radiation emitting source;
 a position sensor for determining a position and an angulation of the detector in relation to the radiation emitting source and a volume of interest, the volume of interest being modifiable by a user; and
 a computational device for integrating the position and angulation of the detector with information as to an energy and a spatial distribution of radiation detected by the detector and deriving a three dimensional representation of the radiation emitting source based on the integration.

19. The system of claim 18 further comprising a graphical user interface for displaying the three dimensional representation.

20. The system of claim 18 further comprising multiple radiation detectors.

21. The system of claim 20, wherein the position sensor is configured to determine a position and an angulation of one or more of the detectors in relation to the volume of interest.

22. The system of claim 20, wherein the computational device is further configured to integrate the position and angulation of one or more of the detectors with information as to the radiation emitting source and a spatial distribution of radiation detected by the respective one or more of the detectors and to derive a three dimensional representation of the radiation emitting source based on the integration.

23. The system of claim 20, further comprising multiple position sensors configured to determine a position and an angulation of each of the multiple radiation detectors in relation to the volume of interest.

24. The system of claim 23, wherein at least one of the multiple position sensors is rigidly affixed to a body of at least one of the multiple radiation detectors.

25. The system of claim 18, wherein the detector is sensitive to gamma radiation.

26. The system of claim 18, wherein the detector is sensitive to electromagnetic radiation.

27. The system of claim 18, wherein the detector is sensitive to particulate radiation.

28. The system of claim 18, wherein the detector is a handheld gamma camera.

29. The system of claim 18, wherein the detector is a Compton camera.

30. A tomographic imaging system comprising:
 a moveable means for detecting radiation from a radiation emitting source;
 a means for determining a position and an angulation of at least one component of the detector means in relation to the radiation emitting source and a volume of interest, the volume of interest being modifiable by a user; and
 a means for integrating the position and angulation of the at least one component of the detector means with information as to an energy and a spatial distribution of radiation detected by the detector means and deriving a three dimensional representation of the radiation emitting source based on the integration.

31. The system of claim 30 further comprising a means for displaying the three dimensional representation as an image or set of images.

32. The system of claim 30 wherein the detector means is sensitive to gamma radiation.

33. The system of claim 30 wherein the detector means is sensitive to electromagnetic radiation.

34. The system of claim 30 wherein the detector means is sensitive to particulate radiation.

35. A tomographic imaging system comprising:
 a moveable detector that is capable of detecting gamma radiation from a gamma ray emitting source, a spatial distribution of the source being not completely known by a user;
 a first position sensor for determining a position and an angulation of the detector in relation to a frame of reference known to selectable by the user; and
 a computational device for integrating the position and angulation of the detector with information as to an energy and a spatial distribution of gamma rays detected by the detector and deriving a three dimensional representation of the gamma ray emitting source with respect to the known frame of reference based on the integration.

36. The system of claim 35, wherein the system is configured to use the determined position and angulation of the detector to estimate the spatial distribution of the gamma ray emitting source with respect to the known frame of reference, and wherein the computational device is configured to use the estimate.

37. The system of claim 36, the computational device being configured to derive the three dimensional representation of the gamma ray emitting source via an iterative reconstruction, wherein the iterative reconstruction includes comparing the estimate of the spatial distribution of the source to the spatial distribution of the gamma rays detected by the detector and modifying the estimate based on the comparison.

* * * * *